United States Patent [19]

Bart de Roos

[11] Patent Number: 4,731,476

[45] Date of Patent: Mar. 15, 1988

[54] PROCESS FOR THE SEPARATION OF L-LEUCINE AND L-ISOLEUCINE

[75] Inventor: Kris Bart de Roos, Ar Hoevelaken, Netherlands

[73] Assignee: Polak's Frutal Works B.V., Amersfoort, Netherlands

[21] Appl. No.: 32,370

[22] Filed: Mar. 31, 1987

[30] Foreign Application Priority Data

Apr. 3, 1986 [GB] United Kingdom ............. 8608179

[51] Int. Cl.$^4$ .............................................. C07C 99/12
[52] U.S. Cl. ..................................... 562/554; 560/155
[58] Field of Search ......................... 562/554; 560/155

[56] References Cited

U.S. PATENT DOCUMENTS 3,960,942  6/1976  Hirsbrunner ..................... 562/554

FOREIGN PATENT DOCUMENTS

| 3318932 | 6/1984 | Fed. Rep. of Germany | 562/554 |
| 3318933 | 6/1984 | Fed. Rep. of Germany | 562/554 |
| 6131550 | 10/1981 | Japan | 562/554 |
| 715572 | 2/1980 | U.S.S.R. | 562/554 |
| 715573 | 2/1980 | U.S.S.R. | 562/554 |

Primary Examiner—Paul J. Killos
Attorney, Agent, or Firm—Dale R. Lovercheck

[57] ABSTRACT

The invention relates to a process for the separation of L-leucine and L-isoleucine. The process is carried out by subjecting a mixture of leucine ester, and isoleucine ester, (or a mixture of leucine ester, isoleucine ester and valine ester) to an esterase catalyzed hydrolysis resulting in a selective hydrolysis of the leucine ester. The pure L-leucine can be isolated from the reaction mixture by first removing the non-hydrolyzed esters by extraction with an organic solvent and then crystallizing the L-leucine at its isoelectric point. The recovered L-isoleucine ester is purified by distillation (if necessary), and hydrolyzed to yield pure crystalline L-isoleucine.

19 Claims, No Drawings

PROCESS FOR THE SEPARATION OF L-LEUCINE AND L-ISOLEUCINE

The invention relates to a process for isolating L-leucine and L-isoleucine from protein hydrolyzates. More particularly, the invention relates to a process for separating L-leucine from mixtures of leucine, isoleucine and valine by a selective esterase catalyzed hydrolysis of the leucine ester in a mixture of esters of these amino acids.

Leucine and isoleucine are isomers with very similar chemical and physical properties. Therefore, their separation is very difficult. One of the earliest processes for separating leucine from isoleucine makes use of the different solubilities of their copper complexes (F. Ehrlich, Ber. 37, 1809 (1904); P. A. Levene and W. A. Jacobs, Biochem. Z. 9, 231, (1908); P. Hirshbrunner and R. Bertholet, Maggi A.G., Ger. Offen. No. 2,417,375 (1975)). Cobalt complexes of leucine and isoleucine can be separated in a similar way. (K. Hayashi and T. Hino, Ajinomoto Co., Japan 15,118 (1962)). Both methods have a few serious drawbacks like the need for quantitative removal of the metal salts from the amino acids, the mother liquors and the waste water.

Leucine and isoleucine can also be separated by selective precipitation with aromatic sulfonic acids. For example, leucine can be isolated by selective precipitation with benzenesulfonic acid or p-toluenesulfonic acid (C. Hongo et al., J. Chem.Technol. Biotechnol. 29, 145 (1979)), Napthalene-2-sulfonic acid (M. Bergmann and W. H. Stein, J. Biol. Chem. 129, 609 (1939); R. D. Hotchkiss, J.Biol.Chem. 141, 171 (1941); D. W. Thomas and C. Niemann, J.Biol.Chem. 175, 241 (1948)) or 2-bromotoluene-5-sulfonic acid (W. H. Stein, J.Biol.Chem. 143, 121 (1942)) and isoleucine by precipitation with p-toluenesulfonic acid (D. M. Hegsted and E. D. Wardwell, J.Biol.Chem. 153, 167 (1944)) or 2-naphthol-6-sulfonic acid (I. Chibata et al., Tanabe Seiyaku Co., Japan Kokai 73 103,515 (1973)). The precipitates have to be purified by repeating recrystallizations. A special problem is the complete removal of the often toxic sulfonates from the end product.

Russian investigators have made use of the different rates of esterification to separate L-leucine from L-isoleucine (I. Kalnins et al, Prikl. Biochem. Mikrobiol. 17, 896 (1981); Chem. Abstr. 96 143287 (1982)). Treatment of a mixture of L-leucine and L-isoleucine with thionyl chloride in ethanol at 60° C. for one hour yielded a mixture of L-leucine ethyl ester and free isoleucine Neutralization and crystallization gave L-isoleucine in pure form. The filtrate was extracted with benzene and the extracted L-leucine ester was hydrolyzed to yield pure L-leucine. Yields of 80-85% of pure L-leucine and L-isoleucine are claimed. In our hands, this method gave substantially lower yields due to the rather poor selectivity of the esterification (see also S. P. Compana Filho and G. Goissis, F. Chromatogr. 236, 197 (1982)).

Moreover, the method has the disadvantage that L-isoleucine is difficult to isolate in pure form if valine is present in the original mixture.

From the European patent application EP No. 22,880 it is known that leucine can be isolated from a mixture of leucine, isoleucine and valine by precipitation at pH 1.5-2.0. From the remaining mother liquor L-isoleucine hydrochloride can be isolated by crystallization from concentrated hydrochloric acid. However, in this way it is not possible to obtain high yields of L-leucine and L-isoleucine in sufficiently high purity for pharmaceutical applications.

The European patent EP No. 26,832 describes a method to isolate isoleucine from a mixture of leucine and isoleucine by treating a solution of the mixture in an anhydrous organic solvent with concentrated hydrochloric acid. The isoleucine precipitates as the hydrochloride salt. To obtain a sufficiently pure product the precipitation with hydrochloric acid has to be repeated.

Finally, the German Pat. DE No. 3,318,933 Cl describes an enzymatic method for the separation of L-leucine and L-isoleucine. The amino acids are acetylated under non-racemizing conditions and the resulting mixture of N-acetyl-L-leucine and N-acetyl-L-isoleucine is treated with hog kidney aminoacylase in the presence of catalytic amounts of $Co^{2+}$. Selective hydrolysis of N-acetyl-L-leucine to L-leucine occurs. The L-leucine crystallizes from the reaction mixture and is filtered off in pure form. The N-acetyl-L-isoleucine in the filtrate is hydrolyzed with hydrochloric acid and the resulting L-isoleucine is collected by fractional crystallization. This process has the disadvantage of requiring the use of a relatively expensive enzyme. Moreover, the process does not allow separation of leucine and isoleucine from valine and phenylalanine, two hydrophobic amino acids which are often present in the leucine/isoleucine fraction from protein hydrolyzates.

The process of this invention consists of the following steps:

(a) esterifying a mixture containing L-leucine and L-isoleucine with an alcohol, (b) selectively hydrolyzing the L-leucine ester by treating an emulsion or solution of said mixture with an enzyme or enzyme-complex having esterase activity and, (c) recovering L-leucine and/or the L-isoleucine ester from the mixture thus obtained.

Depending on the complexity of the starting mixture of amino acids, a purification prior to the enzymatic hydrolysis might be necessary. The mixture of amino acid esters that is subjected to enzymatic hydrolysis preferably does not contain substantial amounts of esters other than those of leucine, isoleucine and valine.

In literature the use of esterases for the enantioselective hydrolysis of L-amino acid esters in mixtures of D- and L-amino acid esters is well known. (See, for example, O. Warburg, Z. Physiol. Chem. 48, 205 (1906) and I. A. Yamskov, et al., Enzyme Microb. Technol 3, 141 (1981)). This allows a simple separation of the resulting L-amino acid from the unaffected D-amino acid ester. However, esterases have not been used for the separation of structural isomers like leucine and isoleucine.

BRIEF SUMMARY OF THE INVENTION

A method of separating L-leucine from a mixture of hydrophobic amino acids, including: providing an amino acid mixture, the mixture comprising L-leucine and L-isoleucine, esterifying the amino acid mixture with an alcohol, to form an ester mixture, the ester mixture including L-leucine ester and L-isoleucine ester, selectively hydrolyzing the L-leucine ester by treating the ester mixture with an enzymatic agent selected from the group consisting of enzyme and enzyme complex having esterase activity to form hydrolysis mixture, the hydrolyzed mixture comprising L-leucine and L-isoleucine ester and separating the L-leucine from the hydrolysis mixture to form purified L-leucine.

DETAILED DESCRIPTION OF THE INVENTION

Suitable starting materials for the isolation of leucine and isoleucine according to the method of this invention can be obtained from many sources. An attractive low-priced starting material is commercial crude leucine, the so-called leucine fraction from protein hydrolyzates, which consists of a mixture of leucine and isoleucine plus small amounts of other amino acids.

In fact, all those protein hydrolyzates that have a sufficiently high leucine and isoleucine content to allow a recovery of these amino acids in reasonable yield, can serve as starting material for the isolation of L-leucine and L-isoleucine. A total content of leucine plus isoleucine representing at least 10% of the total amount of amino acids in the hydrolyzate, is desirable.

A mixture of hydrophobic amino acids (leucine, isoleucine, valine, phenylalanine and/or tyrosine) can easily be separated from protein hydrolyzates by precipitation or extraction. For example, an effective method for separating the hydrophobic amino acids from a protein hydrolyzate consists of counter-current extraction of the aqueous hydrolyzate solution with an alcohol such as n-butanol or isobutanol at pH lower than 2.

The esterification of the mixture of amino acids can be carried out by methods well known in the art. For example, the mixture can be esterified by refluxing in the appropriate alcohol with thionyl or hydrogen chloride. If the mixture is obtained by extraction of a protein hydrolyzate solution with a nonwater-miscible alcohol at pH lower than 2, the esters are prepared by heating the extract. In that case, an additional amount of acid is preferably added to speed up the rate of esterification, while water is removed continuously by heteroazeotrope distillation to drive the esterification to completion.

Purification of the resulting mixture of amino acid esters might be necessary if the starting material was a complex mixture of hydrophobic amino acids. This purification is carried out preferably by flash distillation in vacuo. This yields a distillate containing the esters of valine, leucine and isoleucine and a residue containing the esters of phenylalanine and tyrosine. To avoid heat-induced decomposition of the amino acid esters, the distillation is preferably carried out in a continuous mode, for example, with a film evaporator.

The mixture of amino acid esters containing 30-100% of leucine ester plus isoleucine ester is then subjected to an esterase catalyzed hydrolysis to effect selective hydrolysis of the L-leucine ester.

The hydrolysis is carried out as follows: A 5-50% emulsion of the ester mixture in water is prepared and the pH of the emulsion adjusted to 5-10 by addition of hydrochloric acid or sodium hydroxide solution. In neutral or acid medium a clear solution is usually obtained. The precise pH at which a clear solution is obtained depends on the nature of the esters and their concentration in the reaction mixture. For example, with ethyl esters a clear 20% solution is already obtained at a pH of about 8, but with butyl esters the pH has to be decreased to approximately 7 to dissolve the esters completely. The hydrolysis of the leucine ester is preferably carried out at a temperature between $-5°$ and $60°$ C. in a pH range at which the enzyme displays high activity. Depending on the reaction temperature, and the amount and activity of the enzyme used, the time required for 50-95% leucine ester hydrolysis might vary from less than 1 hour to more than 24 hours.

In this invention the term esterase is used for enzymes capable of catalyzing the hydrolysis of carboxylic acid esters. The term esterase is rather nonspecific and covers a broad range of enzymes including proteinases and lipases. The preferred esterases for the hydrolysis of leucine esters in mixtures with isoleucine esters are the so-called serine proteinases, as, for example, trypsin, chymotrypsin, subtilisin Carlsberg (Subtilisin A, , Alcalase Novo), Subtilisin Novo, Esperase Novo and Pronase, because of their high activity and selectivity. However, other enzymes with esterase activity like the experimental lipase preparation SP 225 of Novo Industri A/S can also be used.

The enzymes are used in purified form or in the form of a crude enzyme preparation. Moreover, it is possible to use the enzymes in the free native form or in an immobilized form. The enzymes can be immobilized, for example, by binding to a solid support, entrapment in a semipermeable polymer gel, or containment in an enzyme membrane reactor. Immobilization has the advantage that the enzyme can easily be reused which might lead to a reduction of the enzyme costs. Moreover, it allows the hydrolysis to be carried out in a continuous mode.

Living microorganisms producing esterase can also be used to catalyze the hydrolysis of leucine esters. The microorganisms can be used either in free or in immobilized form.

The hydrolysis is usually terminated when 70-100% of the original amount of the leucine ester has been converted to L-leucine. The progress of the hydrolysis can be monitored by analyzing the remaining ester fraction by gas chromatography or by determining the released amino acids by high-performance liquid chromatography.

The L-leucine is advantageously isolated from the reaction mixture by adjusting the pH between 8 and 10 and extracting the non-hydrolyzed esters with an organic solvent like, for example, methylene chloride, methyl tert-butyl ether, toluene or a non-water-miscible volatile alcohol. The aqueous solution is then neutralized to pH 6 and concentrated. The crystalline L-leucine that separates is collected by filtration or centrifugation. From nonbuffered reaction mixtures, L-leucine can also be isolated by precipitation with an organic solvent and/or by removing water and nonhydrolyzed amino acid esters by azeotropic distillation in vacuo. The isolation of isoleucine ester from the remaining ester fraction depends on the composition of that fraction. If the fraction contains substantial amounts of valine ester, the esters are first separated, by distillation in vacuo through an efficient distillation column. In contrast with most other amino acid esters, isoleucine and valine esters are quite stable and can be purified by distillation in vacuo without any noticeable decomposition.

The isoleucine esters can be hydrolyzed by methods well known in the art. For example, the esters can be hydrolyzed by refluxing in water, or dilute aqueous acids or by treatment with ammonia or dilute aqueous sodium or potassium hydroxide solution at elevated temperature. Hydrolysis with water or ammonia has the advantage of yielding a solution of isoleucine that is free from salts, thus allowing almost quantitative recovery of L-isoleucine by crystallization.

L-valine ester which is usually obtained as a pure by-product of the purification of the isoleucine ester, can be hydrolyzed in a similar way yielding pure L-valine by crystallization.

The process of this invention has important advantages over other processes for the separation of L-leucine and L-isoleucine:

(a) During the hydrolysis of proteins partial racemization of L-leucine occurs. When leucine is recovered from these hydrolyzates by using the method of this invention optically pure L-leucine is usually obtained because the enzymes selectively catalyze the hydrolysis of the L-leucine ester in mixtures containing both the D- and the L-form.

(b) The enzyme-catalyzed hydrolysis of the amino acid esters is highly selective with respect to the structure of the amino acid, thus allowing a clear separation of leucine from isoleucine.

(c) In comparison with the acylase-catalyzed separation of N-acetyl-L-amino acids, the esterase-catalyzed separation of amino acid esters has the advantage of lower material and enzyme costs. With the process of this invention, very cheap enzymes developed for large-scale application in detergents like, for example, Alcalase 2,4 L or Esperase 8. (both from Novo Industri A/S), are preferably used.

(d) The process of this invention has the advantage of allowing, in addition to the recovery of leucine and isoleucine, the isolation of valine, phenylalanine and tyrosine with a minimum of effort. This is due to the feasibility of separating these amino acid esters by distillation. In practice, this is an important advantage since it often happens that crude leucine fractions isolated from protein hydrolyzates contain substantial amounts of other hydrophobic amino acids.

(e) Due to the distillation and solvent extraction steps involved in their isolation, the recovered amino acids are practically free from heavy metal contaminants.

The purity of the isolated amino acids was controlled by high performance liquid chromatography or by gas chromatographic analysis of volatile derivatives (either the esters or the trifluoroacetylated esters). The optical purity of the isolated amino acids was determined by measuring the specific rotation of a dilute solution of the amino acid in hydrochloric acid or by high-performance liquid chromatography on a chiral stationary phase.

EXAMPLE 1

A mixture of L-leucine (20 g), L-isoleucine (40 g) and L-valine (40 g) in 1250 ml of 3 M HCl in dry isobutanol is refluxed for 6 hours with continuous removal of water by use of an azeotropic column head connected to the reaction vessel via an efficient distillation column. After cooling, ice is added and the pH is adjusted to 9 by cautiously adding 33% sodium hydroxide solution with vigorous stirring. The organic phase which contains about 99% of all amino acid esters is separated from the aqueous phase and concentrated at 200 mm Hg to yield 138 g of an oily residue containing 26.8 g of leucine isobutyl ester, 51.4 g of isoleucine isobutyl ester and 55.0 g of valine isobutyl ester.

To the mixture of isobutyl esters 400 g of water is added and the mixture is stirred vigorously. The resulting emulsion is adjusted to pH 8 by addition of concentrated hydrochloric acid. Alcalase 2,4 L (Novo Industri A/S; 1.00 g) is added and the total weight of the reaction mixture is brought up to 670 g by addition of water. The mixture is then stirred at room temperature for 4 hours during which period 89% of the leucine ester is hydrolyzed.

Sodium hydroxide solution is then added to the reaction mixture till pH is 9 and the nonhydrolyzed esters are removed from the mixture by extraction with methyl tert butyl ether ($2 \times 200$ ml). The aqueous phase is neutralized to pH 6 and concentrated in vacuo until a thick suspension of colourless crystals is separated. The suspension is cooled (ice water) and the crystalline material collected by filtration. Concentration of the mother liquor yields a second crop of crystalline material. After recrystallization of the combined fractions, a total yield of 14.8 g of pure L-leucine is obtained representing 79% of the maximum amount of amino acid that can be recovered from the ester.

Purity by amino acid analysis: 100%
Optical purity by HPLC: 100%

EXAMPLE 2

Example 1 is repeated with the exception that 1.75 g instead of 1.00 g Alcalase 2.4 L is used. After 4 hours at room temperature 94% of the leucine ester is hydrolyzed.

EXAMPLE 3

A mixture of equal amounts of leucine isobutyl ester, isoleucine isobutyl ester and valine isobutyl ester (100 g) is added to 400 g of water and stirred vigorously to obtain a finely dispersed emulsion. Alcalase 0.6 L (3.0 g) is added and the mixture is stirred for 4 hours at room temperature. After that period, 89% of the leucine ester is hydrolyzed. The valine ester is hydrolyzed for only 0.8% and isoleucine ester for less than 0.2%. Isobutanol (50 ml) is added and the L-leucine that precipitates is collected by filtration. The two phases of the filtrate are separated and the aqueous phase is concentrated in vacuo (50 mm) to remove dissolved isobutanol and amino acid esters by azeotropic distillation. During concentration colorless crystals of L-leucine separate. The crystalline material is collected in three crops. The total yield of pure L-leucine is 19.1 g, i.e. 82% of the maximum amount of amino acid that can be recovered from the ester.

$[\alpha]_D^{20} = +15°$ (c=2, 5N HCl).

EXAMPLE 4

Example 3 is repeated with the exception that the enzymatic hydrolysis is carried out at pH 7.2. At this pH the esters are completely dissolved. After 4 hours at room temperature, 88% of the leucine isobutyl ester is hydrolyzed. Valine ester is hydrolyzed for 1.1% and isoleucine isobutyl ester for 0.25%.

EXAMPLE 5

Example 4 is repeated with the exception that Esperase 8.0 L (Novo Industri A/S) is used instead of Alcalase 0.6 L. After 4 hours at room temperature, 86% of the leucine isobutyl ester is hydrolyzed. Valine ester is hydrolyzed for 4.0% and isoleucine ester for 0.64%

EXAMPLE 6

A mixture of equal amounts of freshly prepared leucine n-butyl ester, isoleucine n-butyl ester and valine n-butyl ester (total weight 5 g) is added to 19.85 g of water and stirred vigorously to obtain a finely dispersed emulsion. Alcalase 0.6 L (0.15 g) is added and the mixture is stirred for an additional 4 hours at room temperature. After that period, approximately 68% of the leucine ester is hydrolyzed. The valine ester is hydrolyzed for 1.1% and the isoleucine ester for less than 0.1% Ammonia is added to adjust the pH to 9-9.5 and the nonhydrolyzed esters are extracted with methyl tert-butyl ether. The aqueous phase is concentrated in vacuo (50 mm) to remove ammonia, dissolved organic solvents and amino acid esters by azeotropic distillation. During concentration, colorless crystals of L-leucine separate. The recovery of the L-leucine from the aqueous phase is almost quantitative.

EXAMPLE 7

Example 6 is repeated with the exception that 10 mg of Pronase E (Sigma Chemical Co.) is used instead of 0.15 g of Alcalase 0.6 L. After stirring for 4 hours at room temperature, 89% of the leucine n-butyl ester is hydrolyzed. Isoleucine ester is hydrolyzed for 1.6% and valine ester for less than 0.1%.

EXAMPLE 8

Example 1 is repeated with the exception that instead of isobutanol, sec-butanol is used for esterification. The yield of the esterification is 120 g. The enzymatic hydrolysis of the leucine sec-butyl ester is much slower than the hydrolysis of the corresponding isobutyl ester. After 24 hours at room temperature 59% of the leucine ester is hydrolyzed: 75% of one isomer and 44% of the other (two isomeric esters of each L-amino acid are obtained since racemic sec-butanol is used for esterification)

EXAMPLE 9

A mixture of L-leucine (50 g) and L-isoleucine (50 g) in 1250 ml of 2M methanolic HCl is refluxed for 10 hours. After cooling, ice is added and the pH is adjusted to 9 by cautious addition of a 33% sodium hydroxide solution. The methyl esters are recovered from the aqueous solution by extraction with methylene chloride (3×300 ml). The combined extracts are concentrated at reduced pressure to yield 75 g of a mixture of L-leucine methyl ester and L-isoleucine methyl ester. The enzymatic hydrolysis is carried out as described in example 1. In contrast with the isobutyl esters, the methyl esters are completely dissolved at pH 8. After stirring for 4 hours at room temperature, the leucine ester is hydrolyzed for more than 99%. Recovery of L-leucine from the ester is better than 90%.

EXAMPLE 10

Example 9 is repeated with the exception that instead of methanol, absolute ethanol is used for esterification. The enzymatic hydrolysis of the leucine ethyl ester is complete (i.e. more than 99% has been hydrolyzed) after stirring for 4 hours at room temperature.

EXAMPLE 11

A solution of hydrophobic amino acids in isobutanol obtained by countercurrent extraction of a keratine hydrolyzate at pH 2 is concentrated by distillation at atmospheric pressure to a dry matter content of about 10%.

Concentrated hydrochloric acid is added (1 part on 20 parts of extract) and the solution was further concentrated to a dry matter content of about 25%. To drive the esterification to completion, heating is continued for 6 hours with continuous removal of water by use of an azeotropic column head connected to the reaction vessel via an effective distillation column.

After cooling, ice is added and the pH is adjusted to 9 by cautiously adding sodium hydroxide solution with vigorous stirring. The organic phase which contains about 99% of the hydrophobic amino acid esters is separated from the aqueous phase and concentrated at 200 mm Hg. The residue is subjected to flash distillation to separate the esters of valine, leucine and isoleucine (distillate) from those of phenylalanine and tyrosine (residue).

The distillate has the following approximate composition:
 leucine isobutyl ester—33%
 isoleucine isobutyl ester—21%
 valine isobutyl ester—33%
 proline isobutyl ester—5%
 other minor constituents—8%

To a vigorously stirred emulsion of 100 g of this mixture of amino acid esters in 300 g of water concentrated hydrochloric acid is added till a clear solution is obtained. The pH of the solution is then 7.2. Alcalase 2,4 L (0.75 g) is added and the total weight of the reaction mixture is brought up to 500 g by addition of water. After stirring for 4 hours at room temperature 86% of the leucine ester is hydrolyzed. The reaction mixture is made slightly alkaline (pH about 9) by addition of sodium hydroxide solution and the non-hydrolyzed esters are recovered from the mixture by extraction with tert-butyl methyl ether (2×150 ml). The further procedure is similar to that described in Example 1.

The yield of L-leucine is 16.5 g corresponding to a recovery of 71% from the leucine ester. Purity by amino acid
 analysis: better than 99%
 Optical purity by HPLC: 100%

EXAMPLE 12

The recovered mixture of hydrophobic amino acid esters of Example 11 containing about 35% isoleucine isobutyl ester and 55% valine ester by weight is separated by distillation in vacuo through a 100×1.1 cm Vigreux column equipped with a reflux head. The reflux-discharge ratio is 10:1. The fraction boiling from 53.5° to 56° C. at 1.3 mm Hg contains 90% of the amount of valine isobutyl ester originally present in the mixture and has a purity better than 90%. The fraction collected at 65°-67° C. at 1.3 mm Hg contains about 90% of the amount of isoleucine isobutyl ester originally present in the mixture and has a purity of about 90%. The free amino acids can be recovered from the corresponding esters by acid catalyzed, base catalyzed or autocatalyzed hydrolysis. Base catalyzed hydrolysis is preferred because of its speed and completeness. For example, isoleucine isobutyl ester is hydrolyzed completely after refluxing of a 15% emulsion of the ester in 1N sodium hydroxide solution for 45 minutes. Under these conditions, racemization of isoleucine is about 0.5%.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A method of separating L-leucine from a mixture of hydrophobic amino acids, comprising:
   (a) Providing an amino acid mixture, said mixture comprising L-leucine and L-isoleucine,
   (b) esterifying said amino acid mixture with an alkanol, to form an ester mixture, said ester mixture comprising L-leucine ester and L-isoleucine ester,
   (c) selectively hydrolyzing said L-leucine ester by treating said ester mixture with an enzymatic agent selected from the group consisting of enzyme and enzyme-complex having esterase activity to form hydrolysis mixture, said hydrolyzed mixture comprising L-leucine and L-isoleucine ester and separating said L-leucine from said hydrolysis mixture to form purified L-leucine.

2. The method according to claim 1, wherein said ester mixture is obtained by extraction of a protein hydrolyzate with a nonwater-miscible alcohol at pH lower than 2 to form said extract and said esterifying comprises heating said extract to esterify the L-leucine and L-isoleucine with the alkanol.

3. The method of claim 1-2, wherein said ester mixture is purified by distillation to obtain a fraction consisting essentially of esters of L-leucine, L-isoleucine and L-valine.

4. The method according to claim 1-3, wherein said hydrolysis mixture further comprises non-hydrolyzed esters left after the esterase catalyzed hydrolysis, and further comprising extracting said non-hydrolyzed esters from the hydrolysis mixture by adding alkalinity to said hydrolysis mixture to form an alkaline mixture and extracting said alkaline mixture with an organic solvent to form an extract.

5. The method according to claim 4, wherein L-leucine is recovered from said alkaline mixture by subsequent concentration, neutralization and crystallization.

6. The method according to claim 4, wherein L-isoleucine ester is isolated from the recovered mixture of amino acid esters by subsequently purifying the isoleucine ester by distillation, hydrolyzing the isolated isoleucine ester by refluxing with water, or aqueous acid or alkali, and crystallizing the released L-isoleucine by concentrating and neutralizing the resulting solution.

7. The method of claim 1 wherein amino acid mixture comprises 10-90% by weight of leucine, 10-90% by weight of isoleucine, 0-80% by weight of valine and 0-40% by weight of other amino acids.

8. The method of claim 1-3, wherein said alcohol has from one to ten carbon atoms.

9. The method of claim 1, wherein said enzymatic agent is an esterase.

10. The method of claim 1, wherein the enzymatic agent is a serine proteinase.

11. The method of claim 10 wherein said serine proteinase is chymotrypsin, trypsin, subtilisin Carlsberg (Subtilisin A, Alcalase Novo) subtilisin Novo, Esperase Novo, or Pronase.

12. The method of claim 1 wherein said ester mixture is a 5-50% emulsion of amino acid esters and wherein said emulsion is subjected to enzymatic hydrolysis.

13. The method of claim 1, wherein said ester mixture is a 5-50% solution of amino acid esters and wherein said solution is subjected to enzymatic hydrolysis.

14. The method of claim 1, wherein the hydrolysis is catalyzed by an enzyme in its free native form.

15. The method of claim 1 wherein the hydrolysis is catalyzed by an enzyme in an immobilized form.

16. The method of claim 1 wherein the hydrolysis is carried out batchwise using either a free or immobilized enzyme to catalyze the hydrolysis.

17. The method of claim 1 wherein the hydrolysis is carried out in a continuous mode by sending a solution of amino acid esters through a packed bed of immobilized enzyme.

18. The method of claim 1 wherein the hydrolysis is carried out continuously by using an enzyme membrane reactor that retains the enzyme but lets pass the low molecular weight compounds like salts and amino acids and esters of amino acids.

19. A method of separating L-leucine and L-isoleucine from a mixture of hydrophobic amino acids, comprising:
   (a) Providing an amino acid mixture, said mixture comprising L-leucine and L-isoleucine,
   (b) esterifying said amino acid mixture with an alcohol, to form an ester mixture, said ester mixture comprising L-leucine ester and L-isoleucine ester,
   (c) selectively hydrolyzing said L-leucine ester by treating said ester mixture with an enzymatic agent selected from the group consisting of enzyme and enzyme-complex having esterase activity to form hydrolysis mixture, said hydrolyzed mixture comprising L-leucine and L-isoleucine ester, and separating said L-leucine from said hydrolysis mixture to form purified L-leucine and an L-isoleucine ester mixture to form purified L-isoleucine.

* * * * *

UNITED STATES PATENT AND TRADEMARK OFFICE
CERTIFICATE OF CORRECTION

PATENT NO. : 4,731,476
DATED : March 15, 1988
INVENTOR(S) : de Roos

It is certified that error appears in the above-identified patent and that said Letters Patent are hereby corrected as shown below:

Cover page of patent - Appln. No. " 32,370 "

should read -- 032,370 --

Column 1, line 51 " isoleucine Neutralization "

should read -- isoleucine. Neutralization --

Column 5, line 25 " Esperase 8. "

should read -- Esperase 8.0L --

Signed and Sealed this

Twenty-third Day of August, 1988

Attest:

DONALD J. QUIGG

Attesting Officer     Commissioner of Patents and Trademarks